United States Patent [19]
Kyle et al.

[11] 4,128,686
[45] Dec. 5, 1978

[54] MANAGEMENT OF INCONTINENCE

[76] Inventors: William Kyle, 206 Templestowe Rd., Lower Templestowe, Victoria; Bruce H. Lee, 9, Wimbourne Rd., Mount Waverley, Victoria, both of Australia

[21] Appl. No.: 759,549

[22] Filed: Jan. 14, 1977

[30] Foreign Application Priority Data

Feb. 3, 1976 [AU] Australia .............................. PC4702
Feb. 12, 1976 [AU] Australia .............................. PC4831
Apr. 1, 1976 [AU] Australia .............................. PC5435

[51] Int. Cl.² .................... B32B 5/02; A61F 13/16; B32B 5/06
[52] U.S. Cl. ................................. 428/219; 428/234; 128/290 R; 128/296; 428/300
[58] Field of Search ............... 428/234, 300, 100, 219; 128/290 R, 296

[56] References Cited

U.S. PATENT DOCUMENTS

| 3,301,257 | 1/1967 | Crowe et al. | 428/121 |
| 3,316,669 | 5/1967 | Nachbar | 428/100 |
| 3,545,442 | 12/1970 | Wicker et al. | 428/300 |
| 3,620,894 | 11/1971 | Oates | 128/296 |
| 3,649,429 | 3/1972 | Hughes | 428/300 |
| 3,886,941 | 6/1975 | Duane et al. | 128/296 |
| 3,888,248 | 6/1975 | Moore et al. | 128/296 |
| 4,063,558 | 12/1977 | Smith | 128/290 R |

Primary Examiner—William R. Dixon, Jr.
Attorney, Agent, or Firm—Cushman, Darby & Cushman

[57] ABSTRACT

An assembly for the management of incontinence with an absorbent hydrophilic layer behind a hydrophobic layer. The hydrophilic layer is formed of aligned cellulosic staple fibers of at least 0.5 in length and denier in the range of 2 to 7 in a cross-laid web and needled to form a felt which will absorb at least 350% by weight of urine based upon its dry weight.

19 Claims, 8 Drawing Figures

MANAGEMENT OF INCONTINENCE

The present invention relates to an assembly for providing better care of incontinent patients and maintaining the patient in as dry a condition as possible. Furthermore it protects a bed or chair from being soiled by an incontinent patient. It is particularly applicable to the management of incontinent geriatric adult or paediatric patients and to the management of children suffering from nocturnal eneuresis.

The nursing of incontinent adult patients presents particular problems to hospital staff. Some patients are managed by means of an in-dwelling catheter, but this procedure is not recommended for all patients because there is usually no medical indication for the use of this device, because the use of a catheter frequently results in infection, and because the procedure has no therapeutic effect on the patient. A variety of occlusive appliances (e.g. penile clamps, Vincent appliances, Uridomes (trade mark) and Edwards appliances is available, but such appliances are not fully satisfactory and are not well accepted by elderly or confused patients. It is therefore inevitable in the present state of knowledge that large numbers of patients will continue to be nursed in bed, the nursing care consisting of frequent attention to the patient and frequent changes of the bed linen. The provision of this care imposes strain on the nursing staff involved and on hospital laundering facilities. Further, the need for repeated bed changes and the wetness of bed linen inevitably resulting from incontinence causes aggravation and discomfort to the patient and he or she may also be caused embarrassment which is a serious social problem and may turn the patient into a virtual recluse. The scale of the problem is apparent from an estimate made in Australia that incontinence is responsible for 20% of admissions to geriatric hospital wards and for 10% of the running costs of such hospitals ("Incontinence in the Elderly", Maclaine-Cross A., Proc. Aust. Assoc. Geront., 2(2), 1974, Pages 74–75). A similar situation exists in the United Kingdom and in many other countries.

INTRODUCTION

One way in which incontinent adult patients are nursed in conventional practice may be appreciated from FIG. 1 of the accompanying drawings which shows a typical hospital bed as used for the management of an incontinent adult patient. The bed is shown in the course of making up using the normal lower sheet 1 over which is placed an impermeable rubber or plastics protective sheet 2, and a draw sheet 3 which is usually of heavy-duty cotton drill or a similar material. Over the draw sheet 3 is placed a disposable incontinence pad 4 which consists of several layers of absorbent paper held to an impermeable plastics backing sheet. These disposable incontinence pads suffer from several disadvantages. They are easily saturated and tend to remain wet after passage of fluid which is particularly a disadvantage in the management of elderly or paralysed patients who are prone to develop erythema and may subsequently develop pressure sores. It has been estimated that conventional paper pads fail, in the sense that there is coincidental wetting of the bed, in 65% of cases (F. L. Willington, Nursing Times, Apr. 3rd, 1975, Pages 545–548). Paper pads are liable to disintegrate and stick to the patient's skin which is distressing to the nursing staff who have the job of keeping the patient clean and dry. Confused patients are liable to tear paper pads up. Nevertheless paper incontinence pads are and have been for many years in widespread use despite their acknowledged disadvantages. According to Willington (ibid), the annual consumption in the United Kingdom is estimated to have risen from 25 million pads in 1964 to 62 million pads in 1972 in the hospital service alone. It will therefore be appreciated that there is a need which has existed for many years for a more satisfactory incontinence pad.

BACKGROUND OF THE INVENTION

Figure 1:
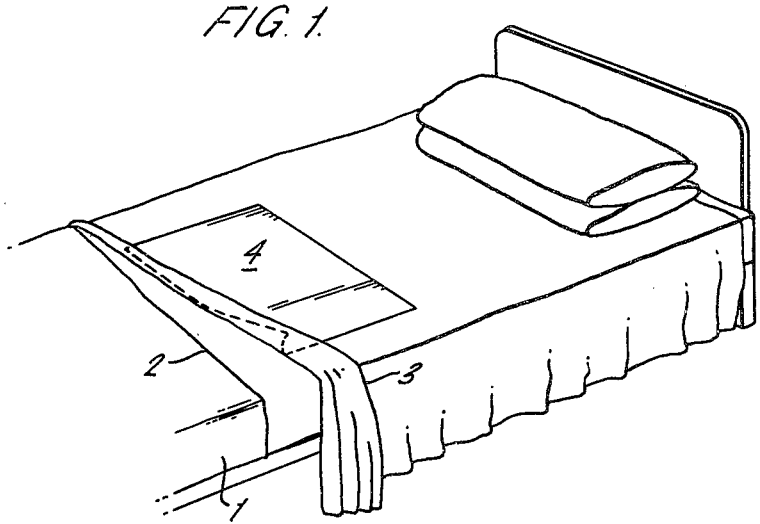
FIG. 1 shows a hospital bed in the course of being made up, and conventional disposable paper incontinence pad.

It has been proposed to manage incontinence by using assemblies comprising a layer of non-absorbent hydrophobic material through which urine can freely pass and at least one layer of absorbent hydrophilic textile material behind the said non-absorbent layer to receive and absorb urine passing through said non-absorbent layer (see, for example, U.K. Pat. Nos. 871435, 1177418 and 1425179, U.S. Pat. Nos. 2905176 and 3523536; French Pat. Nos. 1441872 and 2165001; and Swiss Pat. No. 316547). However, the state of the art at the present time is that, whilst many of the proposed assemblies are satisfactory for disposable diaper use, there does not exist a reliable, reusable and commercially viable assembly to replace paper pads for bed or chair use. In particular, the prior art does not provide a commercially viable assembly which will absorb and retain a substantial amount of urine without reaching saturation under the pressure normally exerted by the patient's body, will substantially retain its strength and cohesion after wetting, through use or laundering, and will disperse urine evenly through the absorbent material away from the site of initial absorption.

OBJECTS OF THE INVENTION

It is therefore an object of this invention to provide an improved assembly for the management of incontinence.

It is also an object of this invention to provide such an assembly which is reliable, reusable and relatively inexpensive.

It is further an object of this invention to provide an assembly which will absorb and retain a substantial amount of urine without reaching saturation under the pressure normally exerted by the patient's will substantially retain its strength and cohesion after wetting, through use or laundering, and will disperse urine evenly through the absorbent material away from the site of initial absorption.

It is a particular object of this invention to provide an assembly to replace paper incontinence pads presently used on beds and chairs.

These objects are achieved by using as the layer of absorbent hydrophilic textile material a layer formed of aligned cellulosic (especially viscose) staple fibres of at least 0.5 inch length and denier in the range 2 to 7 formed into a cross-laid web and needled to form a felt which will absorb at least 350 L % by weight or urine based upon its dry weight and disperse by capillarity urine laterally throughout the felt. It has been found that when the absorbent and non-absorbent layers are separate, a particularly improved assembly is obtained using a brushed nylon non-absorbent layer. Further, it has been found that by forming the specified absorbent layer into an integral needled assembly with a non-absorbent layer of staple polyester fibres and including a plastics scrim, an easily manageable assembly of good structural stability can be obtained.

There have been a number of prior art proposals to use cellulosic staple fibres in incontinence assemblies, particularly diapers, and absorbent surgical dressings. In particular, U.S. Pat. No. 3301257 (Crowe et al) discloses an absorbent surgical dressing formed of sheet material made by laying a web of hydrophilic fibres on one surface of a sheet of cellular sponge material and then passing barbed needles through the web into the sponge sheet to form hydrophilic fibre bundles which extend completely through the cellular sponge sheet. The sponge material is preferably but not necessarily hydrophobic. The hydrophilic fibres are preferably rayon fibres of 0.5 to 3.0 inches length and a denier of 1 to 6. The weight of the fibre web is stated to be less than 5 ozs/yd$^2$ (i.e. 170 g/m$^2$). Dressings are formed by facing two of the sheets together with the fibre web portions of each facing inwardly. There is no teaching that the sheets can be used alone for any purpose and clearly they would be incapable of meeting the absorption and other requirements for incontinence assemblies of the present invention.

U.S. Pat. Specification No. 3523536 (Ruffo) discloses disposable absorbent pads including diapers and underpads comprising a mixture of short non-cardable fibres, such as cotton linters, and long hydrophilic cellulose fibres, such as rayon of 1 to 1.625 inches. The pads are enclosed within a liquid pervious material. However, there is no teaching of improving absorption and durability of the pads by needling cross-laid cellulose fibres in the manner of the present invention. In the illustrated embodiments of Ruffo, the rayon is merely mixed with the short fibres to form an air-laid web.

U.S. Pat. Specification No. 3545442 (Wicker) discloses inter alia an absorbent medical dressing in which a foraminous layer of hydrophobic thermoplastic fibres is connected by an absorbent intermediate layer of, for example, needled cotton wadding, to an absorption layer which preferably is a carded web of rayon fibres of 1 to 2 inches length and about 3 denier. The layers can be united using reciprocating barbed needles which carry hydrophobic fibres into the absorbent layers. The rayon is not cross-laid and the product is intended as a one-use dressing. It would not be suitable for use in the management of incontinence.

U.S. Pat. Specification No. 3888248 (Moore et al) discloses an abdominal pad or surgical dressing in which an absorbent core of, for example, needle punched rayon, is covered with superposed layers of tear-resistant scrim and polyethylene. No details are given concerning the needle punched rayon and there is no teaching that assemblies of the kind disclosed in Moore et al. could be of any use in the management of incontinence. The requirements especially in terms of absorbency are quite different between surgical dressings and incontinence assemblies. The pad or dressing of Moore et al is intended for disposal after use and would not be suitable for the management of incontinence.

French Patent Specification No. 1495510 (Roubane) discloses a pad for sanitary towel use having superimposed non-woven hydrophilic and hydrophobic layers which are needled together. Preferably, the upper layer is polyvinyl chloride and the lower layer is viscose but there is no suggestion that the viscose fibres should be made up into a needle felted layer as in the present invention. The pad of Roubane is, of course, intended for disposal after use.

It will be seen from the foregoing acknowledgement of prior art that, whilst cellulosic fibres and, in particular, rayon have been used or proposed for use in diapers, there has been no previous teachings of or towards the particular needled felt absorbent layer of the present invention. The closest teachings of the use of needled absorbent material are in the related but different field of surgical dressings in which there are only relatively small volumes of fluid to absorb and no reuse requirement. It is believed therefore that the present invention constitutes a substantial and significant advance in the art of incontinence management.

The present invention provides an assembly for the management of incontinence comprising at least one layer of non-absorbent hydrophobic textile material through which urine can freely pass and at least one layer of absorbent hydrophilic textile material behind the said non-absorbent layer or layers to receive and absorb urine passing through the non-absorbent layer or layers, said absorbent layer being formed of aligned cellulosic staple fibres of at least 0.5 inch length and denier in the range 2 to 7 formed into a cross-laid web and needled to form a felt which will absorb at least 350% by weight of urine based upon its dry weight and disperse urine laterally by capillarity throughout the felt.

Preferably, the non-absorbent material is a non-woven felted fabric, especially a needled felt, but it may be fibre-woven, knitted, tuften, woven, or melded. The material may be dyed or undyed. Suitable hydrophobic materials include polyamides, especially nylon, and polyesters which are soft. We have found that a brushed nylon fabric made from a blend of 20/1 monofilament and 40/13 multifilament denier fibres and having a weight of from 50 to 250 g/m$^2$ is particularly satisfactory. The brushed nylon is preferred because the lofting derived from the brushing process is of a suitable density and height to provide a high degree of patient comfort and permeability of urine with resulting dryness to the patient.

The non-absorbent layer can be sewn, bonded, quilted or welded to the needle felted absorbent layer. In one preferred embodiment described hereinafter, the layers constitute an integral construction.

The layer of absorbent textile material consists of cellulosic fibres having a length of at least 0.5 inch (1.27 cm), usually at least 1 inch (2.4 cm) but especially about 1.5 inches (3.8 cm). These fibres are aligned by, for example, garnetting or carding, and formed into a cross-laid web which is then needled to form a felt. Suitably, the web is needled to a scrim or weft support to increase the mechanical strength and dimensional stability of the absorbent layer. Preferably, the scrim is an inert plastics scrim, especially a woven polypropylene scrim.

The absorbent cellulosic needled felt usually has a weight in the range of from 200 to 1000 g/m$^2$, preferably 500–850 g/m$^2$ and especially about 650 g/m$^2$ and a thickness suitably up to 1.25 cm, especially about 0.35 cm. The cellulosic fibres have a weight of from 2 to 7 denier, especially about 2.5 denier. The preferred cellulosic fibre is rayon which can be of various types depending upon the method of manufacture for example, viscose, acetate, cuprammonium. Within the invention the most preferred type is viscose, especially dull viscose.

It is important that the needling be carried out so as to give the absorbent layer a felted structure having an appropriate degree of consolidation and having an appropriate microstructure so that before reaching saturation it takes at least 350% and preferably at least 450% by weight of urine based on the dry weight of the fabric and urine passing into the absorbent layer is dispersed laterally and evenly away from the absorption site by means of capillary action to be retained in the fabric. The capillary action can be supplemented by channelling, for example quilting the absorbent and non-absorbent layers together. Provided that the absorbent material is not saturated the fluid will not escape from its edges and will not escape in undesirable quantities from its front or rear faces on application to the material of a pressure within the range normally encountered in use as a result of a patient sitting or lying on the assembly. It is estimated that the pressure normally exerted by an adult human being in a recumbent position on a bed sheet is about 1.5 lbs per square inch and it is desirable that the weight of fluid released from the fabric on application of such pressure by "wicking back" be no more than 10% of the weight of fluid present in the fabric. Such behaviour is in marked contrast to the behaviour of conventional paper pads or draw sheets where saturation is reached on application of relatively small quantities of fluid to the pad, the surface of the pad remaining moist to the touch and fluid being readily expelled from the pad on application of slight pressure thereto. The preferred density of needle punchings to impart the necessary cohesion and fabric microstructure is between 1500 and 2000 punchings per square inch, especially 1700/in$^2$.

The assembly according to the invention usually will be capable of absorbing and retaining at least 250 ml of fluid and preferably is capable of retaining at least 500 ml of fluid. In the preferred thickness it can have a saturation capacity of about 2500 ml/m$^2$ whereas a conventional paper pad has a saturation capacity of only about 600 ml/m$^2$.

For the management of incontinent adult patients or for the management of nocturnal eneuresis in children the assembly will normally be dimensioned appropriately to fit onto a bed, the dimensions of the absorbent layer ranging from 24 inches to 40 inches widthways and from 24 inches to 40 inches lengthways depending on the prevailing standard sizes of beds. Such absorbent layers will normally have fluid capacities before saturation of approximately 1000 to 3000 ml of fluid which is considerably higher than the range of fluid capacities normally found in disposable paper pads or in conventional draw sheets. The non-absorbent layer usually will be of the same width as the absorbent layer but several inches longer because of the need to ensure that the dryer is at all times in contact with the patient's skin.

When used by a chair-ridden patient the absorbent material is normally used in the form of sheets of width 12 inches to 24 inches and of length 12 inches to 24 inches. Normally several sheets of the absorbent material, typically 3 such sheets, are inserted into an appropriately dimensioned envelope of the non-absorbent material which is then placed on the chair to be protected. Such an assembly will normally have a fluid capacity before saturation of 750 ml or above.

In accordance with one preferred embodiment of the invention, the absorbent and non-absorbent layers are combined in an integral assembly, especially one in which the layers are needle felted together. It has been found that fluid in such an integral fabric is rapidly dispersed into and retained within the absorbent layer and that after a short time the non-absorbent layer feels only slightly moist to the touch, or it may even feel completely dry. Further, the integral assembly usually has greater strength and dimensional stability than corresponding non-integral assemblies (i.e. with separate absorbent and non-absorbent layers).

In the case of the integral needled felted assembly, it is preferred that the non-absorbent layer is of staple fibres, especially polyester fibres, of length at least 0.5 inch, preferably at least 1 inch, of denier from 2 to 7, preferably about 2½, and providing a weight of non-absorbent layer in the assembly in the range of 50 to 300 g/m$^2$, preferably 150 to 200 g/m$^2$ and especially about 170 g/m$^2$. The absorbent layer is preferably of hydrophilic dull viscose rayon staple fibres present in a weight of 200–1000 g/m$^2$, especially 500–800 g/m$^2$, of fibre length at least 0.5 inch and preferably about 1.5 inches and of weight about 2–7 denier, preferably about 2.5 denier. However, a light-weight version of the material may be produced for the management of normally continent patients as an alternative to conventional hospital draw sheets, and in such a light-weight material the non-absorbent layer has a weight of about 50–150 g/m$^2$, preferably about 100 g/m$^2$, and the absorbent layer has a weight of about 200–300 g/m$^2$. Said preferred fibres can be used also in the non-integral assemblies of this invention.

The absorbent fibres are garnetted or carded and formed into a needled cross-laid web and may enclose a scrim of, for example, polypropylene. A web of non-absorbent fibres is placed against one face of the said web to provide the non-absorbent layer after which the assembly is needle punched to give an integral felted fabric of the appropriate degree of consolidation and capillary structure. The integral fabric usually will have a thickness of up to 1.25 cm, preferably 0.5 cm and weigh up to 1350 g/m$^2$.

Advantageously, the webs are laid horizontally and punched by barbed needles. The effect of this needling creates 'pegs' in the fabric, these pegs comprising vertical fibres surrounded by horizontal fibres. Because of the intimacy of contact between the two layers these 'pegs' further assist the dispersion and penetration of the urine into the absorbent layer and together with the scrim if present promote the dimensional stability of the hydrophilic layers.

The horizontal fibres are either ones that have been by-passed by all the needles or are the connecting part of fibres between the 'pegs'. The 'pegs' are created by the needles and their size depends on the size and type of needles, the original web thickness, the amount of needle penetration and the needle density.

Although the polyester or other non-absorbent staple fibre usually will be needled into the rayon or other absorbent staple fibre, the invention includes the reverse process in which the absorbent fibres are needled into the non-absorbent fibres.

The preferred non-absorbent staple fibre for the integral needled assembly is polyester which has a high tensile strength, is hydrophobic and in an especially preferred unitary needle punched form interlaces with the viscose rayon supported by a mesh polypropylene scrim or interlining to form a composite needle punched unitary fabric of a multiplicity of layers.

The assemblies according to the invention may be held in position on the bed or chair by suitable attachment means which may comprise one or more tie cords, patches of VELCRO (trade mark) tape or flaps for tucking in under the mattress of a bed or the cushion of a chair. The said means can be united with the assemblies or with one or more of the constituent layers thereof by sewing or by other convenient means.

A further separate layer of either durable or non-durable hydrophobic urine-permeable fabric may be placed on top of the upper layer to prevent faeces from contacting the assembly of the invention. The further layer should be light in weight and should have interstices fine enough to retain faeces but large enough to allow passage of urine. It may be woven, knitted or melded fabric and may be dyed or undyed.

The absorbent layer of an assembly according to the invention can be treated with an anti-microbial agent such as chlorhexidine, picloxydine and their salts or with an antimicrobial quaternary ammonium compound such as benzalkonium chloride or cetyl pyridinium chloride to impart anti-microbial activity thereto. In service the anti-microbial agent can be applied to the material during routine laundering thereof. It has been found that the use of anti-microbial agents can be helpful in reducing urine odour, although the perceived urine odour when an assembly according to the invention is in use will normally already be much less than when the patient is being managed by conventional nursing techniques. Odour and also the risk of bacterial cross-infection are also serious problems in the laundering of fouled materials and the use of an anti-bacterial agent is helpful in this respect.

An assembly according to the invention may also be subjected to flame-proofing treatment.

An impervious sheet made of, for example, polyethylene or rubber may be placed beneath the absorbent layer to act as a safety barrier in the event of super-saturation. The impervious sheet is preferably, but not necessarily, separate from the non-absorbent and absorbent layers.

DETAILED DESCRIPTION OF THE DRAWINGS

The following is a description by way of example only and with reference to FIGS. 2 to 6 of the accompanying drawings of preferred embodiments of the present invention. In the drawings:

FIG. 1 has been referred to in the introductory passages of this Specification.

Figure 2:
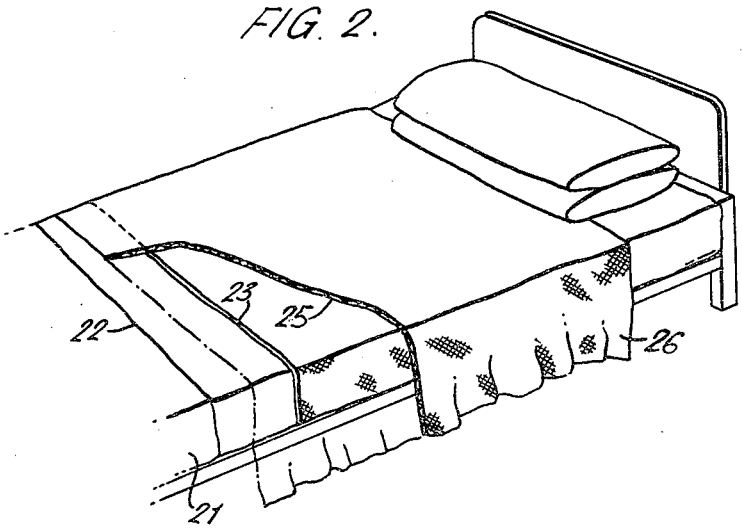
FIG. 2 shows a hospital bed in the course of being made up, and assembly according to the invention being fitted thereto.
Figure 3:
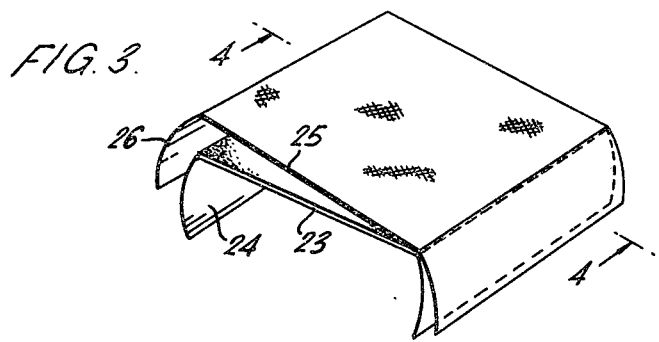
FIG. 3 is a perspective view of the assembly shown in FIG. 2.
Figure 4:
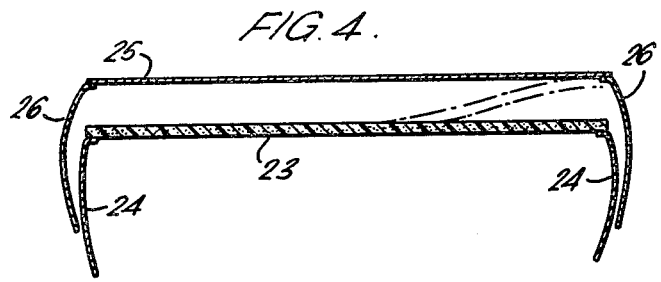
FIG. 4 is a sectional elevational view taken along line 4—4 of FIG. 3.

Referring to FIGS. 2, 3 and 4 a bed is made up with a conventional cotton sheet 21, a conventional liquid-impervious rubber protective sheet 22, an absorbent sheet 23 of needle-felted viscose rayon (see sample A of Example 1) held in position by means of cotton side flaps 24 tucked in under a mattress and an upper sheet 25 of brushed nylon (see sample A of Example 1) has cotton side flaps 26 for tucking in under the mattress. The sheets 23,25 constitute an assembly in accordance with one preferred embodiment of the invention.

The rayon and nylon can be replaced by other hydrophilic and hydrophobic materials respectively of the kinds previously described.

The arrangement shown in FIGS. 2 to 4 has been evaluated in a hospital trial and has been found to keep the patients drier and more comfortable than when previously available techniques of patient management are used, and patients nursed using the said assembly have a lower incidence of erythema of pressure points. They require less frequent changes of bed linen than when conventional nursing techniques are used, and there is reduced urine odour and disturbance of the bedding. The materials used to form the said assembly can be laundered by conventional hospital laundering techniques, and it has been found to date that the laundered fabrics do not suffer from any unusual bacteriological contamination so that there is no added risk of cross-infection when the said assembly is used.

Figure 5:
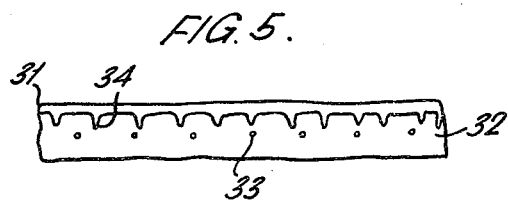
FIG. 5 is a cross-section of an integral needle felted fabric according to the invention.

FIG. 5 shows a cross-sectional view of an integral needle felted fabric according to the invention and which possesses the same advantages in nursing practice as the assembly illustrated in FIGS. 2 to 4. It comprises a layer of polyester fibres 31 and a layer of staple rayon viscose fibres 32 needle punched to a polypropylene mesh scrim 33 (see sample B of Example 1). It may be seen that the effect of needling is to create pegs 34 which extend from the non-absorbent layer 31 into the absorbent layer 32 and whose size depends on the original thickness of the layers, the amount of needle penetration and the needle density. The pegs 34 consist of vertical fibres surrounded by horizontal fibres, which have either been bypassed by the needles or are the connecting parts of fibres between the pegs 34. Because of the intimacy of contact between the layers 31 and 32, the pegs 34 assist penetration and dispersion of fluid through the non-absorbent layer 31 into the absorbent rayon layer 32. The effect of needling the layers 31 and 32 together is that by a "wicking" action fluid is assisted to pass from the non-absorbent layer 31 into the absorbent layer 32 where it is dispersed by capillary action away from the original site. The integral fabric is stronger and also cheaper than a corresponding assembly of two separate fabric layers.

Figure 6:
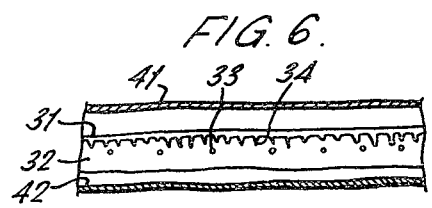
FIG. 6 is a schematic cross-sectional view of the needle felted fabric as shown in FIG. 5 in association with a protective top sheet and an impervious under sheet.

As shown in FIG. 6 the integral fabric of FIG. 5 can be used in association with a non-absorbent fluid-permeable protective sheet 41 and with a fluid impermeable protective base sheet 42.

EXAMPLE 1

A comparison of the absorbent properties of assemblies according to the invention with the properties of conventional materials was carried out using the following samples;

A. An assembly according to the invention of a hydrophobic brushed nylon fabric and a separate needled rayon absorbent fabric having a polypropylene mesh scrim. The nylon fabric was brushed nylon fabric made from a blend of 20/1 monofilament and 40/13 multifilament denier fibres having a weight of about 70 g/m². The rayon fabric was made of 2.5 denier dull viscose rayon fibres having a length of about 1.5 inches. These rayon fibres were carded and formed into cross-laid webs laid up on each side of the polypropylene mesh scrim and then needled at 1700 punchings per sq. inch to form a felt having a weight of about 650 g/m².

B. An integral needled fabric according to the invention having a surface layer of staple polyester fibres and an underlayer of rayon fibres and supported with a polypropylene scrim. The polyester fibres were Dacron (Trade Mark) having a length of about 1 inch and a denier of about 2.5. The rayon fibres were as used in sample A. The fibres were carded and arranged as cross-laid webs with the scrim within the rayon layer and the Dacron on top of said layer. The resultant assembly was needled to form pegs of Dacron depending into the rayon layer. The weight of the Dacron layer was about 170 g/m² and that of the rayon was about 650 g/m².

C. A conventional paper incontinence pad consisting of six layers of a non-needled bonded web of cellulosic fibres held to a liquid-impermeable plastics backing sheet, and D. A conventional disposable baby diaper consisting of a batt of very short flock fibres sandwiched between a paper-like front sheet and a fluid-impermeable backing sheet.

Samples of the above four materials each of dimensions about 4 inches × 4 inches were each treated by means of a syringe with about 25 ml of an aqueous solution of a dyestuff. The water was introduced gradually into the approximate centre of each sample, and the migration of the water could be followed by observing the spread of the dyestuff colour. Each fabric sample was allowed to stand for a period of 5 minutes after which it was noted that in samples A and B the majority of the water had migrated into the absorbent layer which showed very little dye colour and was nearly dry to the touch. No such effect was observed in samples C and D which exhibited persistent surface wetness. The samples were evaluated after standing for five minutes for wetness to the touch, initial run-off of water and retentiveness (judged by whether water could be expelled from the fabric on application of light pressure thereto). The results are shown in Table 1.

TABLE 1

| Sample | Run-Off | Surface Wetness | Retentiveness |
|---|---|---|---|
| A | No | No | Yes (no water expelled) |
| B | No | No | Yes (no water expelled) |
| C | Yes | Yes | No |
| D | No | Yes | No |

These results demonstrate the superiority of the materials according to the invention (Samples A and B) which after wetting had a dry or nearly dry surface and showed high absorption capacity with no run-off. These results were strikingly different from those obtained using Samples C and D where after wetting the surface was very moist to the touch, water could be readily expelled on light pressure and rapid loss of strength, resulting in disintegration of non-woven fabric was observed.

EXAMPLE 2

The speed of absorption of water into the absorbent layer of an assembly according to the invention was evaluated using the needle-felted fabric consisting of rayon fibres needle-bonded to a polypropylene mesh scrim of sample A of Example 1. The speed of absorption of fluid, the rate of spread of absorbed fluid and the total fluid absorption were evaluated as follows and were compared with the values for a conventional paper disposable pad and with a conventional artificial nursing sheepskin formed from synthetic fibres.

SPEED OF ABSORPTION OF FLUID AND RATE OF SPREAD OF ABSORBED FLUID

A 10 cm length of polystyrene tubing of inside diameter 2 cm with an attached weight of 100 g was positioned vertically on a suitable size sample in the centre of a marked 13 cm circle and 30 ml of water containing the indicating dyestuff yellow FCS C.1. (1957) 15985 was added to the tube. The speed of absorption was measured as the time for the tube to empty to pad level and the rate of spread was measured by the time taken for the fluid to spread to 13 cm diameter.

TOTAL FLUID ABSORPTION

The total fluid absorption was measured by an adaption of ASTM method D 461-72 by totally immersing the weighed dried pad in water at 37° C. for one minute, placing the pad on absorbent paper and rolling it twice with a standard 1 kg roller. The total fluid absorption was recorded as the weight of retained fluid expressed as a percentage of the dry pad weight.

TABLE 2

| Test Material | Speed of Absorption | Rate of Spread | Total Capacity | Total Fluid Absorption |
|---|---|---|---|---|
| Unwashed pad* (6.5g/100 cm²) | 32 sec. | 87 sec. | — | — |
| Hand washed pad* (6.5g/100 cm²) | 19 sec. | 35 sec. | 3050 ml/ 650 g pad | 470% |
| Hospital Laundered pad* (6.5g/100 cm²) | 17 sec. | uneven | 2630 ml/ 650 g pad | 445% |
| Disposable Paper pad | 15 sec. | 30 sec. | less than 200 ml (run off) | — |
| Acrylic Sheepskin (20" × 13") | 13 sec. | 80 sec. | 1940 ml/ 543 g pad: (run off) | 370% |

*Rayon fabric of sample A of Example 1.

It was found in the above test that although the initial speed of absorption of fluid by the needle-felted rayon pad was entirely satisfactory, the speed of absorption is improved after initial washing, and that this improved speed of absorption is retained after further washings. The needle felted rayon pad was capable of withstanding repeated washing although better results were obtained when a blanket wash precedure was followed than when a linen wash was followed. Both paper pad and the acrylic sheepskin type pad were unsatisfactory inter alia because of run off. It will be appreciated that in absorbent material according to the invention, the absorbed fluid spreads laterally away from the site of initial absorption by capillary action and is thereafter retained within the fabric.

EXAMPLE 3

A study was carried out with the object of evaluating the assembly of the invention as a replacement for conventional nursing techniques in the management of incontinent adult patients. The subjects of the study were 32 female terminal geriatric and psychiatric patients in a single hospital ward. The patients were divided into groups of 10, 11 and 11 patients who were nursed in rotation by the treatments described in the following three groups:

TREATMENT A

An arrangement according to the invention was used which consisted of the assembly of sample A of Example 1. The layer presented to the patient's body was the brushed nylon fabric measuring 36 inches × 42 inches with the brushed side uppermost. The layer beneath was an underlay of the absorbent needled rayon fabric measuring 36 inches × 38 inches. Both the top layer and the under layer were provided with mercerised cotton flaps 18 inches wide to tuck in under the mattress and hold the assembly in position. Underneath the absorbent layer was a waterproof sheet. The general arrangement was shown in FIG. 2.

TREATMENT B

The patients were treated as in Group A except that the pad of absorbent needled rayon fabric was treated with 20 ml of RESIGUARD (Trade Mark) (an antimicrobial agent containing 1% picloxydine and and 12% benzalkonium chloride).

TREATMENT C

Following conventional practice a draw sheet made of heavy cotton drill was folded and placed under each patient. Disposable paper pads were not used because the hospital concerned considered them generally less satisfactory than draw sheets alone.

The study was of 21 nights duration, the patients being rotated so as to spend seven nights in each of the groups A, B and C. The nursing staff were instructed to examine the patients at regular two hourly intervals and to assess the need to change the patient's bed linen on the basis of the perceived dryness of the patient's skin and also having regard to the condition of the bed linen and the apparent comfort of the patient. The reasons for any change of bed linen were recorded, and the patients were evaluated for skin dryness and for erythema of pressure points. The presence or absence of urine odour and wrinkling or other similar disturbance of the bed linen were also recorded.

The number of changes of bedding and the interval between changes is recorded in Table 3.

TABLE 3

| Treatment | No. of Patients | No. of Hours Exposed | No. of Inspections | No. of Changes | Mean Interval Hours Between Changes | Changes Per 100 Inspections |
|---|---|---|---|---|---|---|
| A | 32 | 2830 | 1039 | 243 | 11.6 | 23.4 |
| B | 32 | 2864 | 1024 | 293 | 9.8 | 28.6 |
| C | 32 | 2994 | 1051 | 657 | 4.6 | 62.5 |

It will be appreciated from the figures given in Table 3 that patients being managed using an assembly according to the invention require changing of their bed linen on average at intervals of 10.6 hours compared to an average of 4.6 hours when using cotton draw sheets alone. The patients benefit from the new technique by having more restful and less disturbed sleep periods because it is impossible to avoid arousing patients from sleep during change of their bed linen. The reduced frequency of changes was also regarded by the nursing staff as a considerable and welcome reduction to their workload.

Table 4 indicates the number of occasions on which the skin of each patient in each group was noted as being damp, dry or wet. Because of the poor urine absorption of draw sheets patients on this treatment had wet skins more often than patients being treated according to the invention even though the draw sheets were under each patient for a shorter period than when the assembly according to the invention was used.

TABLE 4

| Treatment | No. of Times Dry | Skin Recorded As *Damp | Wet | Total No. of Observations |
|---|---|---|---|---|
| A | 292 | 458 | 226 | 976 |
| B | 359 | 381 | 264 | 1004 |
| C | 386 | 1 | 659 | 1046 |

*Attributed by nursing staff as being perspiration on the patient's skin.

Table 5 shows the observations for erythema of the pressure points and of urine odour. It will be seen that the use of an assembly according to the invention gives a much reduced incidence of both urine odour and of erythema. An additional reduction of urine odour is noted when the antibacterial agent is present in the layer of absorbent material. A reduced incidence of wrinkling and other disturbance of the bed linen is also noted from the results quoted in Table 5.

TABLE 5

| Treatment | Erythema (%) Present | Urine Odour (%) Observed | Wrinkling (%) Noted |
|---|---|---|---|
| A | 6.4 | 5.3 | 14.3 |
| B | 7.8 | 2.5 | 7.9 |
| C | 37.8 | 26.7 | 40.9 |

The study revealed that the materials used according to the invention can readily be laundered using conventional hospital equipment and procedures. It was found that they were best laundered using non-ionic detergents and using temperatures up to 65° C. i.e. the same washing and rinsing procedures as are used to launder woollen blankets. It was estimated that the life of the absorbent and the non-absorbent fabrics would exceed 12 months in normal use, and that no significant loss of urine absorption capacity is to be expected over this period, although some slight shrinkage of the soaker underlay could be observed.

By "cellulosic fibres" as used in this Specification, we mean absorbent fibres made from cellulose or having the same absorption characteristics as absorbent fibres made from cellulose.

Figure 7:
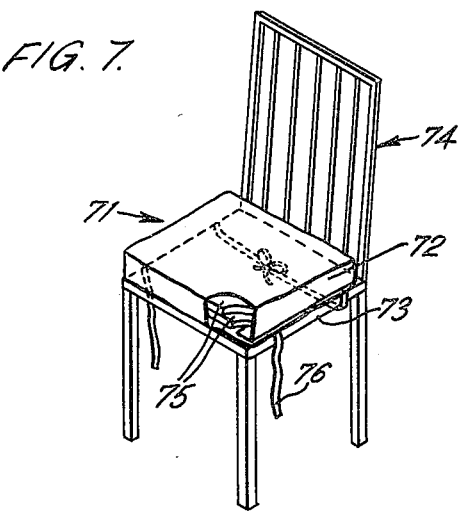
FIG. 7 is a perspective view partly in section of an assembly of the invention in the form of a chair cover.
Figure 8:
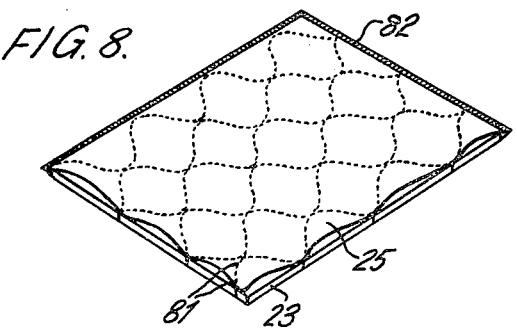
FIG. 8 is a perspective view partly in section of a quilted two layer assembly of the invention.

The invention is further illustrated in FIGS. 7 and 8.

Referring to FIG. 7, a chair cover 71 comprises a pillow-case type envelope 72 of hydrophobic brushed nylon fabric dimensioned to cover the seat 73 of a chair 74. The envelope 72 contains two separate layers 75 of a needled rayon absorbent fabric. Ties 76 are provided on the envelope 72 to secure the cover 71 to the chair 74. The fabrics preferably are as specified for sample A of Example 1.

FIG. 8 shows an assembly essentially identical to that of FIGS. 3 and 4 but in which the layers 23 and 25 are quilted together by means of stitching 81 and are bound together at their edges by stitching 82.

It will be appreciated that the invention is not restricted to the details described above and that numerous modifications and variations in those details can be made without departing from the scope of the invention as claimed hereinafter.

We claim:

1. In an assembly for the management of incontinence comprising at least one layer of non-absorbent hydrophobic textile material through which urine can freely pass and at least one layer of absorbent hydrophilic textile material behind the said at least one non-absorbent layer to receive and absorb urine passing through the said at least one non-absorbent layer, the improvement comprised in that the abosrbent layer is formed of aligned cellulosic staple fibers of at least 0.5 inch length and denier in the range 2 to 7 formed into a cross-laid web and needled at 1500 to 2000 punchings per square inch to form a felt which will absorb at least 350% by weight of urine based upon its dry weight and will disperse urine laterally by capillarity throughout the felt.

2. The assembly of claim 1 wherein the said felt weighs in the range 200 to 1000 g/m$^2$.

3. The assembly of claim 2 wherein the cellulosic staple fibres have a length of at least 1 inch and the said felt weighs in the range 500 to 850 g/m$^2$.

4. The assembly of claim 2 wherein the cellulosic staple fibres have a length of about 1.5 inches and a denier of about 2.5 and the said felt weighs about 650 g/m$^2$.

5. The assembly of claim 1 wherein the cellulosic staple fibres are rayon fibres.

6. The assembly of claim 1 wherein the needle punching is carried out at about 1700 punchings per square inch.

7. The assembly of claim 1 wherein the staple fibres are needled to a scrim or weft support.

8. The assembly of claim 7 wherein the scrim is a woven polypropylene scrim.

9. The assembly of claim 1 wherein the hydrophobic material is a brushed nylon formed of a blend of 20/1 monofilament and 40/13 multifilament denier fibres and has a weight of 50 to 250 g/m$^2$.

10. The assembly of claim 1 wherein the absorbent and non-absorbent layers are combined as an integral needle felted material.

11. The assembly of claim 10 wherein the hydrophobic material is formed of staple fibres of at least 0.5 inch length and denier in the range 2 to 7 needle felted into a hydrophobic layer having a weight in the range 50 to 300 g/m$^2$.

12. The assembly of claim 11 wherein the hydrophobic fibres are of at least 1 inch length and a denier of about 2.5 and the felted layer thereof weighs 150 to 200 g/m$^2$.

13. The assembly of claim 11 wherein the hydrophobic fibres are polyester fibres.

14. The assembly of claim 1 wherein the absorbent and non absorbent layers are quilted together.

15. The assembly of claim 1 adapted for use on a bed and having attachment means for holding the assembly in position on the bed.

16. The assembly of claim 1 adapted for use on a chair and having attachment means for holding the assembly in position on the chair.

17. The assembly of claim 16 wherein the hydrophobic material is formed into an envelope to cover a chair seat and at least one layer of the absorbent material is inserted into the envelope.

18. An assembly for the management of incontinence comprising a non-absorbent urine-permeable layer of a brushed nylon formed of a blend of 20/1 monofilament and 40/13 multifilament denier fibres and having a weight of 50 to 250 g/m$^2$, a scrim-reinforced urine-absorbent layer formed from viscose rayon staple fibres having a length about 1.5 inches and a denier of about 2.5 by forming aligned fibres into a cross-laid web and needling the web into a woven polypropylene scrim to form a felt having a weight of rayon of about 650 g/m$^2$.

19. An assembly for the management of incontinence comprising an integral needle felted material having an upper non-absorbent urine-permeable layer of polyester fibres of at least 1 inch length and of about 2.5 denier and a weight of about 170 g/m$^2$ needled to a urine-absorbent layer formed from viscose rayon staple fibres of about 1.5 inch length and about 2.5 denier by forming aligned fibres into a cross-laid web and needling the web into a woven polypropylene scrim to form a felt having a weight of rayon of about 650 g/m$^2$, in which pegs of substantially vertical polyester fibres surrounded by substantially horizontal polyester fibres extend into but not through the rayon layer.

* * * * *